(12) United States Patent
Yoo

(10) Patent No.: US 7,397,561 B2
(45) Date of Patent: Jul. 8, 2008

(54) SPECTROSCOPY SYSTEM

(75) Inventor: Woo Sik Yoo, Palo Alto, CA (US)

(73) Assignee: WaferMasters, Incorporated, San Jose, CA (US)

( * ) Notice: Subject to any disclaimer, the term of this patent is extended or adjusted under 35 U.S.C. 154(b) by 0 days.

(21) Appl. No.: 11/505,661

(22) Filed: Aug. 16, 2006

(65) Prior Publication Data

US 2007/0103682 A1  May 10, 2007

Related U.S. Application Data

(63) Continuation-in-part of application No. 11/268,148, filed on Nov. 7, 2005.

(51) Int. Cl.
| | | |
|---|---|---|
| *G01J 3/36* | (2006.01) | |
| *G01J 3/44* | (2006.01) | |
| *G01N 21/63* | (2006.01) | |
| *G01N 21/65* | (2006.01) | |

(52) U.S. Cl. ........................... 356/328; 356/343
(58) Field of Classification Search ................. 356/328, 356/343
See application file for complete search history.

(56) References Cited

U.S. PATENT DOCUMENTS

| 4,810,091 | A | | 3/1989 | Sullivan |
| 5,479,258 | A | | 12/1995 | Hinnrichs et al. |
| 5,638,173 | A | | 6/1997 | Smith et al. |
| 5,713,364 | A | * | 2/1998 | DeBaryshe et al. ......... 600/476 |
| 5,886,784 | A | * | 3/1999 | Engelhardt ................... 356/326 |
| 5,986,758 | A | | 11/1999 | Lyons et al. |
| 6,285,019 | B1 | * | 9/2001 | Engelhardt et al. .......... 250/216 |
| 6,483,103 | B2 | * | 11/2002 | Engelhardt et al. .......... 250/226 |
| 6,510,001 | B1 | * | 1/2003 | Engelhardt et al. .......... 359/385 |
| 6,555,811 | B1 | * | 4/2003 | Amos ......................... 250/234 |
| 6,677,566 | B2 | * | 1/2004 | Knebel et al. ............. 250/201.3 |
| 6,809,815 | B2 | * | 10/2004 | Knebel ........................ 356/308 |
| 6,903,816 | B2 | * | 6/2005 | Nakata et al. ................ 356/318 |
| 6,914,238 | B2 | * | 7/2005 | Engelhardt et al. .......... 250/234 |
| 6,977,724 | B2 | * | 12/2005 | Knebel ........................ 356/317 |
| 7,092,086 | B2 | * | 8/2006 | Knebel ........................ 356/301 |
| 2004/0057047 | A1 | * | 3/2004 | Knebel ........................ 356/301 |

FOREIGN PATENT DOCUMENTS

| EP | 0 862 055 | 2/1998 |
| WO | WO 03073082 | 9/2003 |

* cited by examiner

*Primary Examiner*—Gregory J. Toatley, Jr.
*Assistant Examiner*—Bryan Giglio
(74) *Attorney, Agent, or Firm*—Jeffrey A. Hopkins; MacPherson Kwok Chen & Heid, LLP.

(57) ABSTRACT

Systems and techniques for improved spectroscopy. In some embodiments, mechanical and/or optical zoom mechanisms may be provided for monochromator systems. For example, movable detector systems allow a detector to be positioned with respect to a dispersive element in order to obtain a first resolution. The detector systems may then allow the detector to be positioned with respect to a dispersive element to obtain a second different resolution. In some embodiments, spectroscopy of a first sample region may be performed using a plurality of excitation wavelengths. Multiple detectors may be positioned to receive light associated with different ones of the plurality of excitation wavelengths.

21 Claims, 7 Drawing Sheets

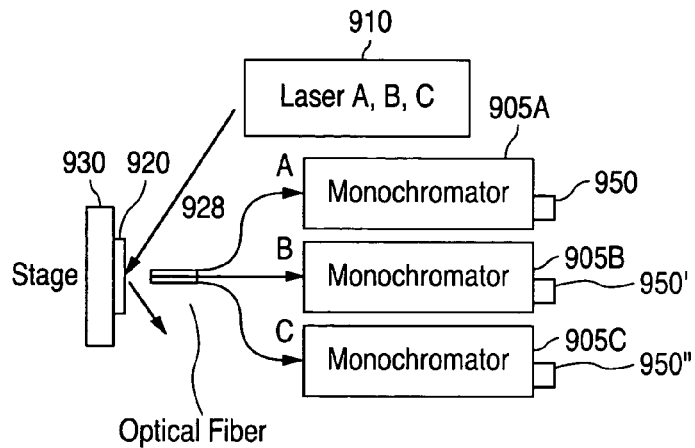
FIG. 9A
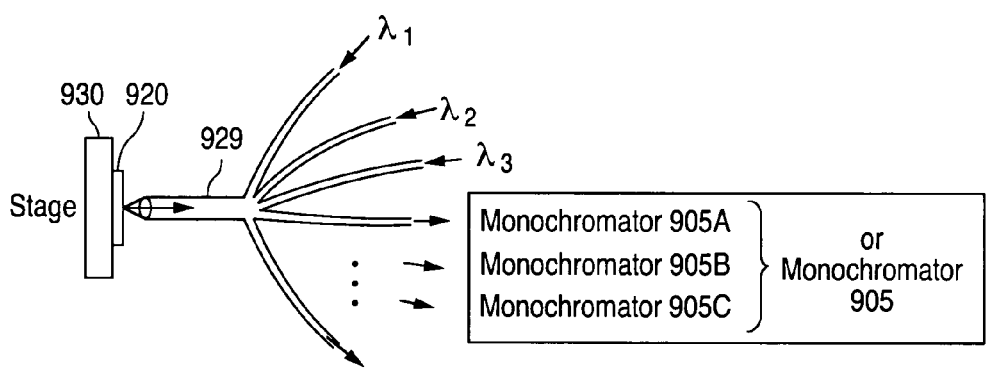
FIG. 9B
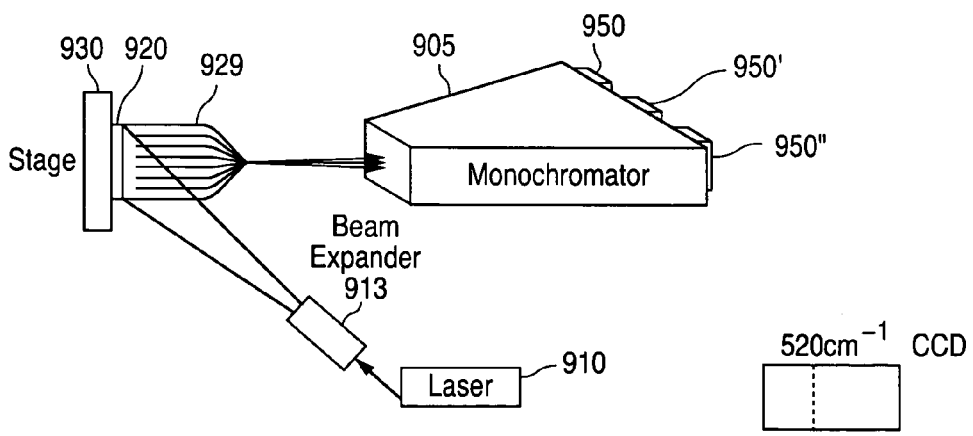
FIG. 9C  FIG. 9D

US 7,397,561 B2

SPECTROSCOPY SYSTEM

CROSS REFERENCE TO RELATED APPLICATION

This application is a continuation-in-part of U.S. patent application Ser. No. 11/268,148 filed on Nov. 7, 2005, which is hereby incorporated by reference in its entirety.

BACKGROUND

1. Field of Invention

This invention generally relates to spectroscopy, particularly to monochromator systems for spectroscopy (e.g., for Raman spectroscopy).

2. Related Art

A number of techniques may be used to obtain information about materials. One technique that may be used is Raman spectroscopy. In Raman spectroscopy, laser light is incident on a surface of a material to be analyzed. Most of the light scatters elastically from the surface (which is referred to as Rayleigh scattering). However, some of the light interacts with the material at and near the surface and is scattered inelastically due to excitation of vibrational, rotational, and/or other low-frequency modes of the material. The inelastically scattered light is shifted in wavelength with respect to the incident laser light, either down in frequency (corresponding to the excitation of a material mode by the incident photons, also referred to as Raman Stokes), or up in frequency (corresponding to the interaction of the incident photons with an already-excited material mode, also referred to as an anti-Stokes Raman). The amount of the shift is independent of the excitation wavelength, and the Stokes and anti-Stokes lines are displaced from the excitation signal by amounts of equal magnitude.

Raman spectroscopy is performed by detecting the wavelength-shifted light. In order to detect light of a particular wavelength of interest, such as Raman-shifted laser light, a spectroscopy system includes a monochromator.

FIG. 1 shows a simplified example of a Raman spectroscopy system 100, according to the prior art. A laser source 110 illuminates a sample 120 mounted on a stage 130. Light 115 reflected from sample 120 includes elastically scattered light (which may be referred to as Rayleigh scattered light), as well as inelastically (Raman) scattered light. In order to isolate the Raman scattered light, system 100 includes a monochromator 105, including a diffraction grating 140, a filtering mechanism such as a notch filter 155 and/or slit 107, and a fixed detector 150. In order to analyze different regions of sample 120, stage 130 may be used to provide relative movement of the sample with respect to the incoming light.

Light 115 is incident on a rotatable diffraction grating 140, which disperses the light according to its wavelength. In FIG. 1, the relative position of grating 140 and detector 150 is selected to detect a desired wavelength $\lambda_d$, but not to detect other wavelengths $\lambda_1$, $\lambda_2$, and $\lambda_3$. Because the Raman shift is relatively small, system 100 also includes a notch filter 155 positioned before detector 150 and configured to filter the strong Rayleigh scattered component at the excitation wavelength.

Different detector types may be used. In older spectroscopy systems, photomultiplier tubes (PMTs) were common. However, PMTs integrate the optical signal received on the entire detector surface. By contrast, newer spectroscopy systems generally use array detectors such as charge coupled device (CCD) array detectors, complementary metal oxide semiconductor (CMOS) detectors, and photodiode array detectors.

In order to detect the desired wavelength (and/or to scan a number of wavelengths), some existing systems rotate diffraction grating 140, while detector 150 is fixed. For example, if wavelengths $\lambda_1$, $\lambda_2$, and $\lambda_3$ are of interest, diffraction grating 140 may be rotated to scan the range of wavelengths shown in FIG. 1.

For existing spectroscopy systems, the wavelength resolution for a particular measurement (i.e., the data collected at a particular rotation angle of diffraction grating 140) is fixed.

One way in which prior systems could be used to obtain more data about particular wavelength ranges of interest was to scan the light across the detector by rotating diffraction grating 140. For a low resolution system, a user could first scan the wavelengths rapidly, by rotating diffraction grating 140 through a first angular range at a first speed. After identifying the wavelength ranges of interest, the user could perform one or more additional scans. By performing the scans at a slower speed (and usually for a smaller angular range), the resolution of the spectroscopy can be increased.

SUMMARY

In general, in one aspect, a spectroscopic system includes a dispersive element (such as a fixed or rotatable reflective diffraction grating, transmissive diffraction grating, prism, or other dispersive element) positioned to receive incoming light comprising a plurality of wavelengths and to transmit wavelength-dispersed light. The system further includes a detector configured to receive at least a portion of the wavelength-dispersed light, wherein the at least a portion of the dispersed light comprises divergent dispersed light. The system further includes a moveable detector mount (such as a motorized rotation and linear translation stage) configured to position the detector to receive a desired portion of the divergent dispersed light, and wherein the detector is mounted to the moveable detector mount. The moveable detector mount (e.g., motorized rotation and linear translation stage), may include a controller configured to receive signals indicative of a desired position of the detector, and to position the detector to receive the desired portion of the divergent dispersed light at the desired position.

The moveable detector mount may be configured to position the detector at a pre-determined optical path length from the dispersive element to obtain a pre-determined resolution. The detector may be positioned at a first pre-determined optical path length from the dispersive element to obtain a first resolution, and then positioned at a second pre-determined optical path length from the dispersive element to obtain a second resolution. The second resolution may be higher than the first resolution, and the second optical path length may be greater than the first optical path length.

The moveable detector mount may be configured to position the detector at a first position having a first pre-determined angular relationship to the dispersive element, and further configured to position the detector at a second position having a second different pre-determined angular relationship to the dispersive element.

The system may further be configured to perform depth profiling using light of different excitation wavelengths. For example, the plurality of wavelengths may include a first excitation wavelength and a second excitation wavelength. The system may be configured to move the detector mount to a first position associated with the first excitation wavelength and to obtain spectroscopic data indicative of one or more physical characteristics of a first sample region to a first depth. The system may be configured to move the detector mount to a second position associated with the second excitation wavelength, and to obtain spectroscopic data indicative of the one or more physical characteristics of the first sample region to a second different depth. The first position associated with the first excitation wavelength may comprise a position to receive Raman shifted light from the first sample region, wherein the Raman shifted light comprises inelastically scattered light incident on the first sample region at the first excitation wavelength.

The plurality of wavelengths may include a first excitation wavelength and a second excitation wavelength, and the system may further comprise another detector configured to receive at least a portion of the divergent dispersed light. The system may include another moveable detector mount configured to position the another detector to receive a different desired portion of the divergent dispersed light. The another detector may be mounted to the another moveable detector mount. The desired portion of the divergent dispersed light may comprise light associated with the first excitation wavelength, while the different desired portion of the divergent dispersed light may comprise light associated with the second excitation wavelength.

The dispersive element, the detector, and the moveable detector mount are included in a monochromator. The system may further comprise a sample mount and a light source configured to generate light at a first excitation wavelength. The light source may be positioned to transmit light at the first excitation wavelength to a sample mounted on the sample mount, and the dispersive element may be positioned to receive light scattered from the sample in response to receiving the light at the first excitation wavelength. The light scattered from the sample may comprise Rayleigh scattered light and Raman scattered light.

The system may further comprise a light stopper adjacent to the detector. The light stopper may be configured to allow light at a first excitation frequency to be received in the detector at a first time, and further configured to substantially prevent light at the first excitation frequency from being received in the detector at a second different time. The system may further comprise a movement mechanism configured to position the light stopper away from the detector at the first time.

The system may include one or more additional optical elements. For example, the system may further comprise a curved mirror positioned to receive light reflected from a surface and to reflect the received light as to the dispersive element as incoming light. The system may further comprise a second mirror, the second mirror configured to receive dispersed light from the dispersive element and to reflect the received dispersed light as divergent dispersed light.

In general, in another aspect, a monochromator system may include a dispersive element configured to receive light including a plurality of wavelengths and to disperse the plurality of wavelengths according to wavelength. The system may further comprise a controller configured to receive information indicative of a desired spectroscopic resolution and to generate one or more signals indicative of the desired spectroscopic resolution. The system may further comprise a zoom mechanism comprising at least one of an optical zoom mechanism and a mechanical mechanism, wherein the zoom mechanism includes at least one element moveable with respect to the dispersive element. The zoom mechanism may be in communication with the controller and may be configured to move the at least one element in response to receiving the one or more signals indicative of the desired spectroscopic resolution.

For example, the zoom mechanism may comprise a mechanical zoom mechanism including a detector mount moveable with respect to the dispersive element. The detector mount may include a position controller configured to receive the one or more signals indicative of the desired spectroscopic resolution and to move the detector mount to a position associated with the desired spectroscopic resolution.

In another example, the zoom mechanism may comprise an optical zoom mechanism including at least one moveable optical element, and wherein the optical zoom mechanism is configured to receive the one or more signals indicative of the desired spectroscopic resolution and to move at least the one moveable optical element relative to the dispersive element to a position associated with the desired spectroscopic resolution. The monochromator system may include a detector configured to receive Raman shifted light scattered from a sample.

In general, in another aspect, a monochromator system may comprise an optical system configured to receive light scattered from a first region of a sample surface in response to receiving light at a plurality of excitation wavelengths and to disperse the received light according to wavelength. The system may further comprise a first detector mounted to a first moveable detector mount and a second detector mounted to a second moveable detector mount. The first moveable detector mount may be configured to move the first detector to a first position associated with a first excitation wavelength of the plurality of excitation wavelengths. The second moveable detector mount may be configured to move the second detector to a second position associated with a second different excitation wavelength of the plurality of excitation wavelengths.

The first detector may be further configured to detect a received portion of light scattered from the first region of the sample surface in response to receiving light at the first excitation wavelength at a first time, while the second detector may be further configured to detect a received portion of light scattered from the first region of the sample surface in response to receiving light at the second excitation wavelength at the first time.

The optical system may comprise a dispersion element selected from the group consisting of a transmissive diffraction grating, a reflective transmission grating, and a prism. The received portion of light scattered from the first region of the sample surface in response to receiving light at the first excitation wavelength at the first time may include divergent light or substantially parallel light.

The first detector may further be configured to receive light scattered from at least a second region of the sample surface in response to receiving light at the first excitation wavelength at the first time. The optical system may include a first optical fiber positioned to receive light scattered from the first region of the sample surface and a second optical fiber positioned to receive light scattered from the second region of the sample surface.

The first detector may comprise an array detector such as a detector selected from the group consisting of a CCD array detector, a photodiode array detector, and a CMOS detector. The optical system may include a flat mirror configured to reflect divergent light to be received in the first detector.

The light scattered from the first region of the sample surface in response to receiving light at the first excitation wavelength at the first time may be scattered from a portion of the first region of the sample surface extending downward a first depth, while the light scattered from the first region of the sample surface in response to receiving light at the second excitation wavelength at the first time may be scattered from a portion of the first region of the sample surface extending downward a second depth different than the first depth. The system may thus be configured to generate a depth profile of the sample.

In general, in another aspect, a spectroscopy method may include receiving information indicative of a first desired resolution for a spectroscopy measurement. The method may further include positioning at least a portion of a zoom apparatus relative to a dispersive element based on the first desired resolution. The method may further include obtaining first spectroscopy data having the first desired resolution with the detector. The method may further include receiving information indicative of a second desired resolution for a spectroscopy measurement and positioning the at least a portion of a zoom apparatus relative to the dispersive element based on the second desired resolution. The method may further include obtaining second spectroscopy data having the second desired resolution with the detector.

The method may further include receiving information indicative of a first desired wavelength range for the spectroscopy measurement, the first desired wavelength range extending from a first extremum wavelength (i.e., a minimum or maximum of the range) to a second extremum wavelength (the other of the minimum or maximum of the range). The method may further include positioning the detector relative to the dispersive element based on the first extremum wavelength, and obtaining first spectroscopy data having the first desired resolution with the detector may comprise scanning the detector relative to the dispersive element from the position based on the first extremum wavelength to a position based on a second extremum wavelength.

The method may further include receiving information indicative of a second desired wavelength range for the spectroscopy measurement, the second desired wavelength range extending from an initial extremum wavelength to a final associated extremum wavelength. The second desired wavelength range may be smaller than the first desired wavelength range. The method may further include positioning the detector relative to the dispersive element based on the initial extremum wavelength. The spectroscopy method may be a Raman spectroscopy method.

In general, in another aspect, a spectroscopy method may include generating excitation light comprising a plurality of substantially discrete excitation wavelengths including a first excitation wavelength and a second excitation wavelength. The method may further comprise scattering the excitation light from a first region of a sample and dispersing the scattered light according to wavelength. The method may further comprise receiving a first portion of the dispersed light at a first detector positioned to receive light associated with the first excitation wavelength and receiving a second different portion of the dispersed light at a second detector positioned to receive light associated with the second excitation wavelength. The method may further comprise determining one or more characteristics of the first region of the sample based on the first portion and the second portion.

Scattering the excitation light from a first region of a sample may comprise scattering light having the first excitation wavelength from a first depth of the first region of the sample, and may further comprise scattering light having the second excitation wavelength from a second different depth of the first region of the sample. The method may further comprise determining one or more characteristics of the first region of the sample based on the first portion and the second portion comprises generating a depth profile of the first region of the sample. The depth profile may comprise data indicative of one or more physical characteristics of the first region of the sample at the first depth and data indicative of one or more physical characteristics of the first region of the sample at the second depth.

These and other features and advantages of the present invention will be more readily apparent from the detailed description of the exemplary implementations set forth below taken in conjunction with the accompanying drawings.

BRIEF DESCRIPTION OF THE DRAWINGS

FIGS. 9A and 9B are top views of embodiments of a spectroscopy system to detect multiple wavelengths;

FIG. 9C is a perspective view of an embodiment of a spectroscopy system to detect multiple wavelengths;

FIG. 9D is an illustration of a CCD display for spectroscopy of multiple locations of a sample;

Like reference symbols in the various drawings indicate like elements.

DETAILED DESCRIPTION

Systems and techniques provided herein may allow for more flexible spectroscopy than provided by existing spectroscopy systems.

For optical spectrometers, monochromators are used to isolate particular wavelengths or wavelength ranges of interest. Typically, a user selects a particular monochromator based on the anticipated application. For example, for Raman spectroscopy applications, bulky high resolution monochromators are generally used, to obtain high resolution data for the Raman peaks of interest. For other applications, a user may wish to choose a compact and easy to use low resolution monochromator.

In order to provide enhanced flexibility, systems and techniques provided herein include monochromator and spectrometer designs with zoom in/zoom out capability. As a result, both low and high resolution spectroscopy may be performed.

Figure 1:
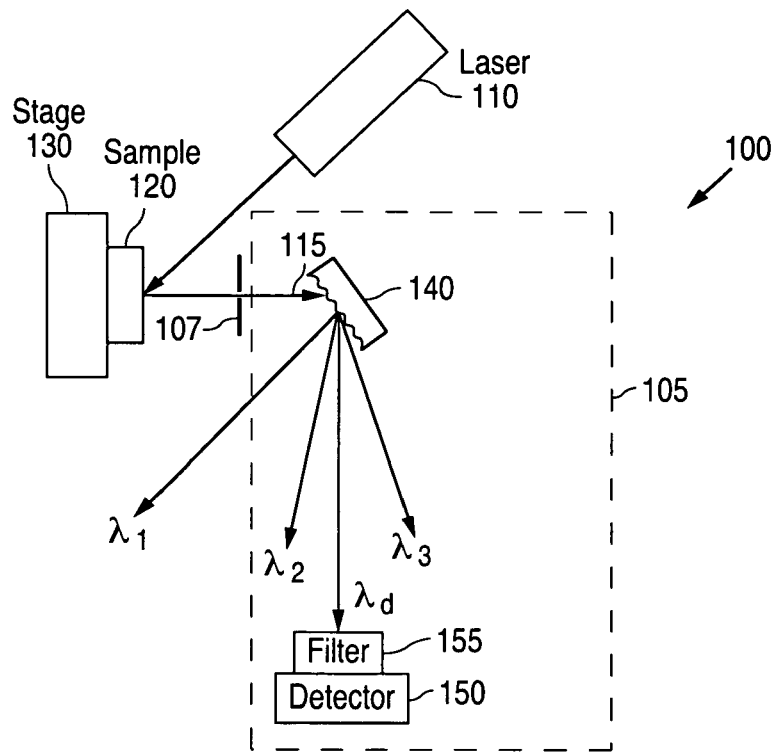
FIG. 1 is a top view of a Raman spectroscopy system, according to the prior art.
Figure 2:
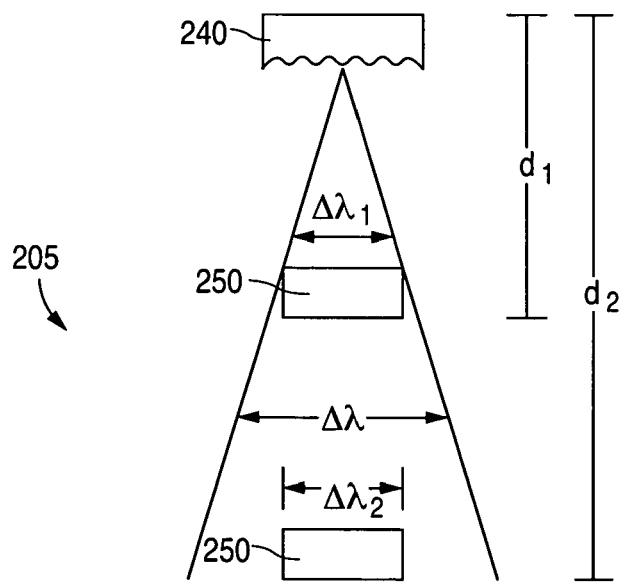
FIG. 2 is top view of a monochromator.

FIG. 2 is a top view of a monochromator 205 illustrating the way in which the resolution of system 200 depends on the distance between diffraction grating 240 and detector 250, for divergent light incident on detector 250.

When detector 250 is positioned at a distance $d_1$ that is relatively close to diffraction grating 240, it captures light from a relatively large solid angle. This provides a low resolution "view" of the material (i.e., a relatively large wavelength range of the reflected light). However, when detector 250 is positioned at a distance $d_2$ that is relatively far from diffraction grating 240, it captures light from a relatively small solid angle. The captured light includes a narrower wavelength range, providing a higher resolution view of the material.

Figure 3:
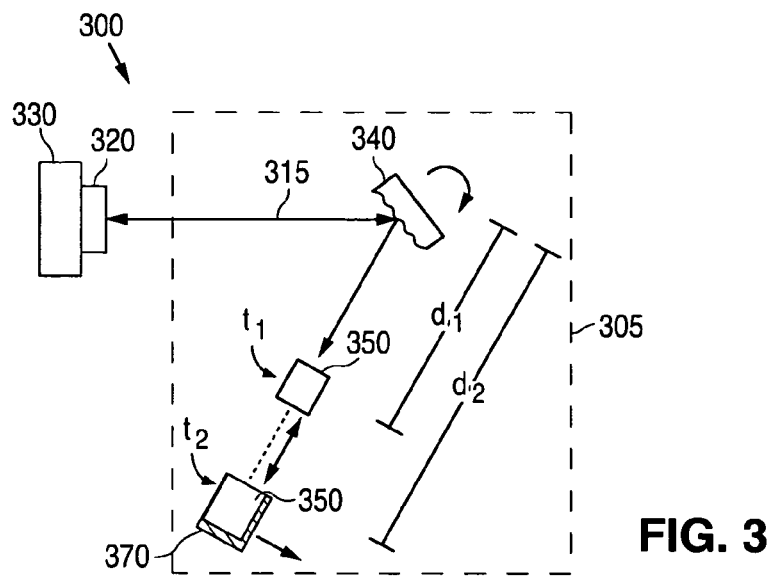
FIG. 3 is a schematic top view of a spectroscopy system, according to some embodiments.

FIG. 3 shows a diagram of a spectroscopy system 300 incorporating zoom in/zoom out capability, according to some embodiments. System 300 includes a sample 320 mounted on a stage 330, and a monochromator system 305. Monochromator system 305 includes a wavelength dispersion mechanism such as a diffraction grating 340 that is configured to disperse including light 315 according to wavelength. Monochromator 350 also includes a movable detector 350. A user may control the position of movable detector 350 in order to obtain the desired spectral resolution. For example, the user may provide one or more parameters indicative of a desired positioning to the spectroscopy system via a user interface such as a computer, and one or more controllers of system 300 (not shown) may position detector 350 based on the one or more parameters. In some embodiments, a user may position detector 350 at least partially using one or more manual controls (e.g., knobs, levers, or other manual control elements).

For example, at a first time $t_1$ detector 350 may be positioned at a distance $d_1$ from diffraction grating 340, and detector 350 may obtain low resolution data of sample 320. The low resolution data may be analyzed to determine one or more wavelength regions of interest. At a later time $t_2$, detector 350 may be positioned at a different distance $d_1$ from diffraction grating 340, and detector 350 may obtain high resolution data of sample 320 (or of a different sample requiring higher resolution data).

Monochromator 305 may also be configured to provide relative angular displacement between diffraction grating 340 and detector 350. The relative angular movement may be used to align detector 350 as desired (e.g., to capture Raman-shifted light) and/or to scan the beam across detector 350. Relative angular motion may be provided by rotating detector 350 about diffraction grating 340, while diffraction grating 340 is fixed. Instead (or in addition), diffraction grating 340 may be rotated. Additionally, as noted above, dispersive elements other than reflective diffraction gratings may be used, such as transmittance gratings or prisms.

Embodiments in which diffraction grating 340 is fixed may be particularly beneficial for some applications. For example, in some spectroscopy systems, a number of additional optical elements (such as flat mirrors, curved mirrors, etc.) may be used with grating 340. Incorporating a moveable detector 350 may allow for enhanced ease of use. Rather than moving elements of the optical system to detect a signal at the wavelength of interest, the user need only calculate the dispersion angle of the wavelength of interest and/or determine the desired resolution, and position detector 350 accordingly.

Detector 350 may be moved in a number of ways. For example, detector 350 may be mounted on a stage 370 to provide the desired movement (e.g., radial and/or angular movement). In some embodiments, stage 370 may be a motorized rotation and linear translation stage. The stage may include a controller configured to receive signals indicative of a desired position of stage 370 and to move the stage in response to the received signals.

System 300 may also include an inlet slit (not shown). Narrow inlet slits may be used to improve the resolution, but may also reduce the amount of light that is available for detection. Larger inlet slits increase the amount of light available for detection, but the resolution may be less than desired.

Figure 4A:
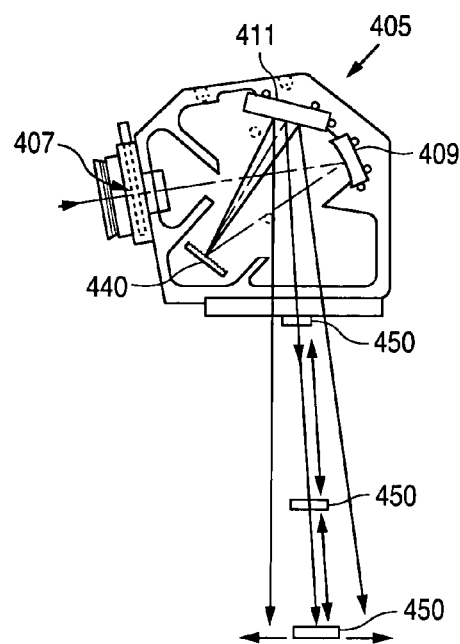
FIG. 4A is a top view of a monochromator system, according to some embodiments.

FIG. 4A shows an embodiment of a monochromator system 405. System 405 receives light (including light to be analyzed) through an input slit 407 (which may have a width selected for the particular application, as noted above). The light is reflected from a curved mirror 409 and is then incident on a dispersive element such as a transmittance grating 440. The dispersed light is reflected from a flat mirror 411. Different portions of the reflected light may be received by a detector 450, which may be a CCD array detector, a photodiode array detector, complementary metal oxide semiconductor (CMOS) detector, or other type of detector.

Note that some existing systems use a similar optical system to that shown in FIG. 4A, except that instead of flat mirror 411, a curved mirror is used. In those systems, the dispersed light reflects of the curved mirror as parallel beams of light that differ in wavelength across their extent. By replacing the curved mirror with flat mirror 411, the dispersed light diverges so that capturing the light at different distances allows for measurements having different resolution.

Figure 4B:
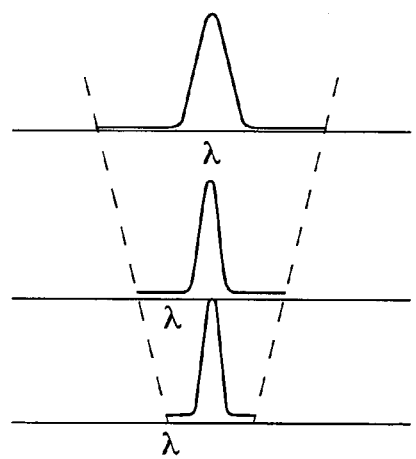
FIG. 4B illustrates the resolution differences for three different radial positions of a detector in a spectroscopy system.

FIG. 4B illustrates the different resolutions that may be obtained at three different radial positions of detector 450. At a first position closest to mirror 411 (and thus with the shortest optical path length to diffraction grating 440), a low resolution spectrum may be obtained, containing a wide wavelength range. At a second position farthest from mirror 411, a high resolution spectrum, containing a narrow wavelength range, may be obtained. At a third, intermediate position, a medium resolution spectrum may be obtained.

Figure 4C:
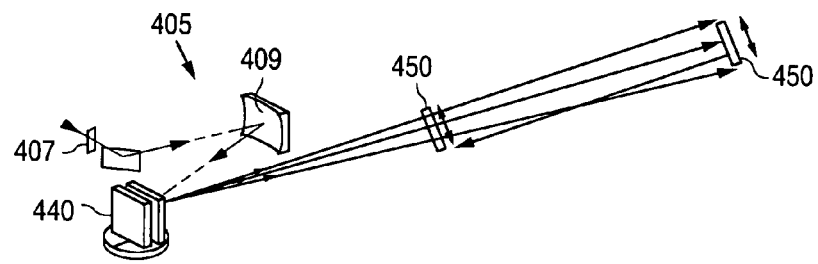
FIG. 4C is a perspective view of a monochromator system, according to some embodiments.

FIG. 4C is a perspective view of another embodiment of a monochromator 405. Monochromator 405 includes an entrance slit 407 for receiving light from a sample. The received light is incident on curved mirror 409, and then dispersed by grating 440. In contrast to the monochromator of FIG. 4A, flat mirror 411 is omitted. The dispersed light is incident on a detector 450, which may be positioned closer to grating 440 for lower resolution or farther from grating 440 for higher resolution.

In some embodiments, optical zoom in/zoom out capability may be used instead of or in addition to the mechanical zoom in/zoom out capability described above and illustrated in FIGS. 3, 4A, and 4C. For example, a monochromator may include a fixed detector, with one or more optical elements positioned between the dispersion element and the detector. The one or more optical elements may include a first fixed lens and a second moveable lens, so that the dispersion of the light is increased (zoom in, for increased resolution), or decreased (zoom out, for decreased resolution) at the detector. In some embodiments, commercial zoom in/zoom out lens assemblies for camera systems may be used. However, for applications in which the wavelengths used are unduly absorbed by glass, other lens materials may be needed. For example, quartz or other UV compatible materials may be needed.

As noted above, in previous spectroscopy systems, a notch filter may be used to filter out the strong Rayleigh scattered laser signal, so that the Raman signal may be analyzed. However, for a system incorporating a moveable detector, such as the systems shown in FIGS. 3 and 4A and described above, a different technique may be used, which may provide both easier and more accurate spectroscopy calibration.

For Raman spectroscopy, the difference in wavelength between the excitation wavelength $\mu_{exc}$ and the Raman wavelength $\lambda_{Raman}$ may be designated as $\Delta\lambda$. In order to efficiently and accurately determine $\lambda_{Raman}$, the Rayleigh scattered signal at $\lambda_{exc}$ may be used to calibrate the position of detector 550.

For example, detector 550 may initially be positioned at a distance from diffraction grating 540 so that both Rayleigh scattered light and Raman scattered light can be captured across the breadth of detector 550 (e.g., the resolution is low enough so that both signals may be detected at the same time). Detector 550 may be moved angularly with respect to grating 540, until the strong Rayleigh scattered signal is detected and positioned on detector 550 so that the Raman scattered light is also captured by detector 550. Note that the relative positions of the Raman and Rayleigh scattered light depend on whether the Stokes line, the anti-Stokes line, or both are to be detected.

Once detector 550 is positioned, a light stopper 552 may be moved into position by an actuator 554 (e.g., a micrometer), until the Rayleigh scattered light is sufficiently blocked. The resulting Raman peak may then be captured using detector 550. This may provide for more accurate spectroscopy, because the Raman peak is measured with respect to the position of the detected Rayleigh peak, which serves as a wavelength reference for the measurement.

Figure 5:
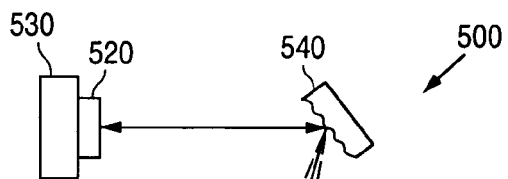
FIG. 5 is a top view of an embodiment of a spectroscopy system.

The ability to rotate detector 550 angularly with respect to grating 540, as illustrated in FIG. 5, may also be used to perform spectroscopy at multiple wavelengths. This may provide a significant benefit, since different wavelengths of light penetrate the sample to different depths. Larger wavelengths penetrate deeper into a material, while smaller wavelengths interact with the sample material closer to the sample surface. As a result, using multiple wavelengths at the same time allows for a depth profile of the material to be obtained.

Figure 6:
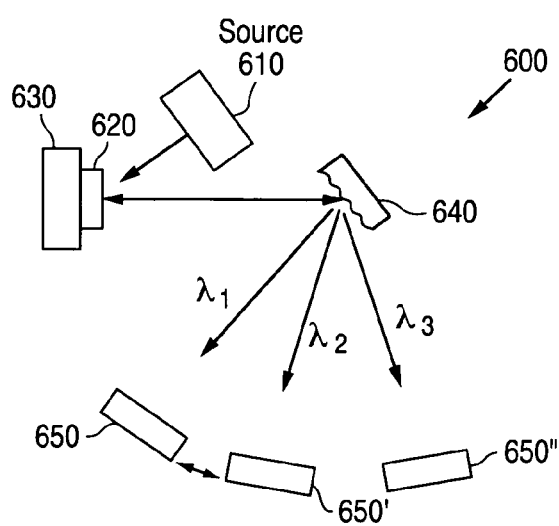
FIG. 6 is a top view of an embodiment of a spectroscopy system to detect multiple wavelengths.

FIG. 6 shows a top view of a simplified spectrometry system 600 that may be used to perform spectrometry at multiple wavelengths. A light source 610 provides excitation light having more than one wavelength. For example, light source 610 may be a laser (such as an argon ion laser) that generates light at multiple excitation wavelengths, or may comprise multiple lasers generating light at multiple wavelengths. In FIG. 6, signals with three wavelengths $\lambda_1$, $\lambda_2$, and $\lambda_3$, corresponding to three different excitation wavelengths are dispersed by grating 640. In some embodiments, a single moveable detector 650 may be positioned angularly with respect to a diffraction grating 640 to detect each of the wavelengths $\lambda_1$, $\lambda_2$, and $\lambda_3$ in turn. In other embodiments, three different detectors 650, 650', and 650" may be positioned to detect each of the wavelengths $\lambda_1$, $\lambda_2$, and $\lambda_3$ at the same time.

By contrast, in some existing systems, the diffraction grating is rotated so that the wavelength of interest is incident on a fixed detector. In such systems, obtaining sample data at multiple wavelengths may be complicated. For example, a first set of sample data may be obtained at a first wavelength using a first light source. The light source may then be changed, and a second set of sample data obtained at a second wavelength. However, the system needs to be calibrated for the new light source, and the second set of data correlated with the first set. Thus, existing systems may be both more complex and less accurate than using simultaneous excitation of the sample with multiple wavelengths.

Figure 7:
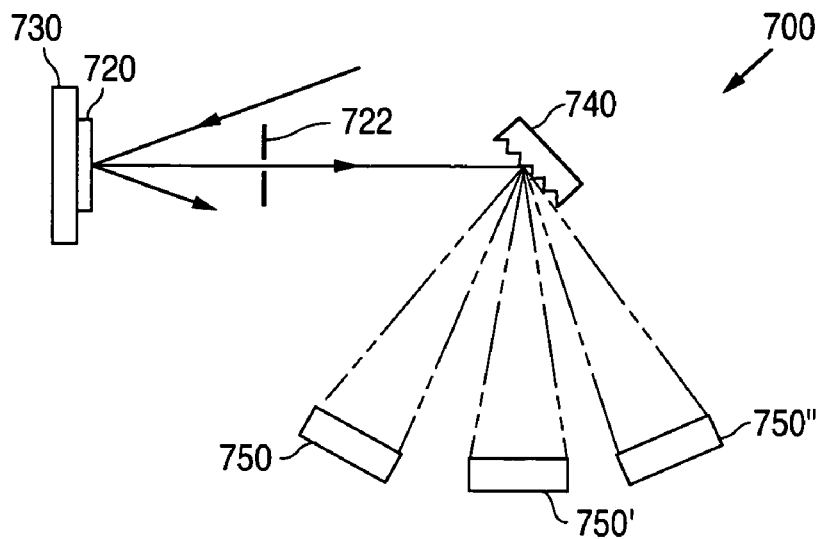
FIG. 7 is a top view of another embodiment of a spectroscopy system to detect multiple wavelengths.

FIG. 7 shows another implementation of a system 700, which may provide a better signal to noise ratio for Raman scattered light. System 700 includes a slit 722 so that specularly scattered light is not incident on detectors 750, 750', and 750." A collimated beam is incident on grating 740, which disperses the light according to wavelength. FIG. 7 illustrates and example where three wavelengths of interest are detected in detectors 750, 750', and 750" (although of course different numbers of detectors may be used).

Figure 8:
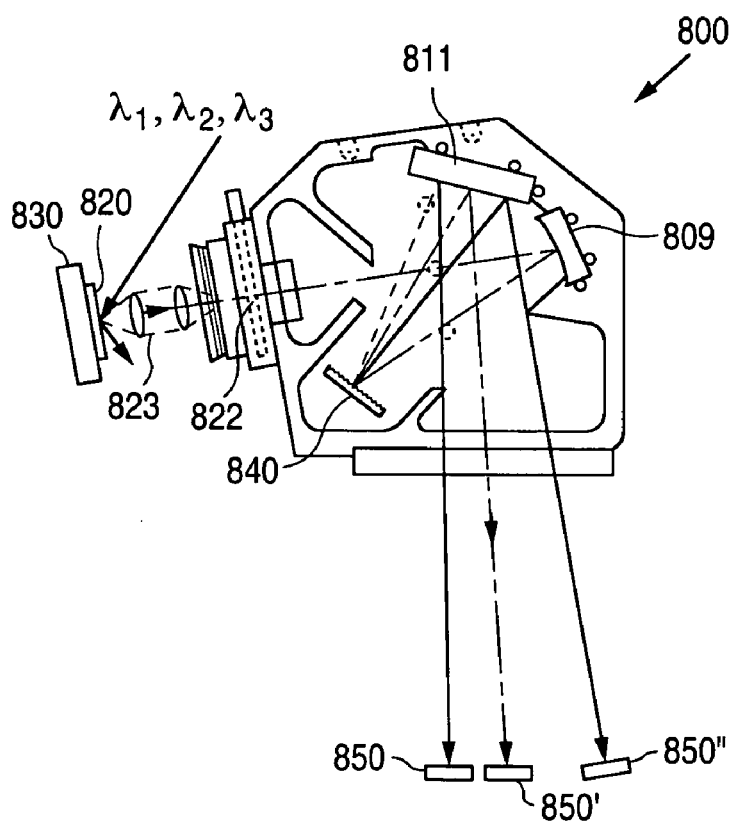
FIG. 8 is a top view of another embodiment of a spectroscopy system to detect multiple wavelengths.

FIG. 8 shows another implementation of a system 800 for multiple wavelength excitation of a sample 820 mounted on a stage 830. Light reflected from sample 820 may first be incident on one or more optical elements 823, which may focus the light from sample 820 to be transmitted through a slit 822. The light may then be reflected from a mirror 809 to a diffraction grating 840. The dispersed light may then be reflected from a flat mirror 800, and the wavelengths of interest may then be detected in detectors 850, 850', and 850." As with the implementation of FIG. 4A, flat mirror 811 may be omitted in some embodiments.

FIGS. 9A to 9C show different implementations of systems that may be used to obtain depth profiling information using one or more monochromators 905. For example, in FIG. 9A, light from one or more lasers 910 includes a plurality of excitation wavelengths (e.g., three different wavelengths). The light is incident on sample 920, which is mounted on stage 930. Reflected light is incident on one or more optical fibers 928, and transmitted to separate monochromators 905A, 905B, and 905C, which have associated detectors 950, 950', and 950." In FIG. 9B, light reflected from sample 920 on stage 930 is received in a fiber bundle 929 comprising a plurality of optical fibers. The wavelengths of interest are then transmitted to separate monochromators 905A, 905B, and 905C, or to a single monochromator 905 configured to detect multiple wavelengths.

In FIG. 9C, a larger area of sample 920 may be analyzed at a particular time by incorporating a beam expander 913 after light source 910. A fiber bundle 929 may receive light from different regions of sample 920, and transmit the light to multiple monochromators, or to a single monochromator 905 having multiple associated detectors such as detectors 950, 950', and 955." A spectroscopy system such as that shown in FIG. 9C may be particularly useful for the semiconductor industry. When sample 920 is a semiconductor sample such as a silicon wafer, different regions of the wafer (e.g., 9 different regions corresponding to 9 fibers in fiber bundle 929) may be analyzed at one time. FIG. 9D shows an example of a CCD output corresponding to simultaneous Raman spectrometry of multiple regions of the wafer. As FIG. 9D shows, detector pixels corresponding to each of the sample regions shows a signal corresponding to the 520 $cm^{-1}$ Raman shift of silicon.

Figure 10:
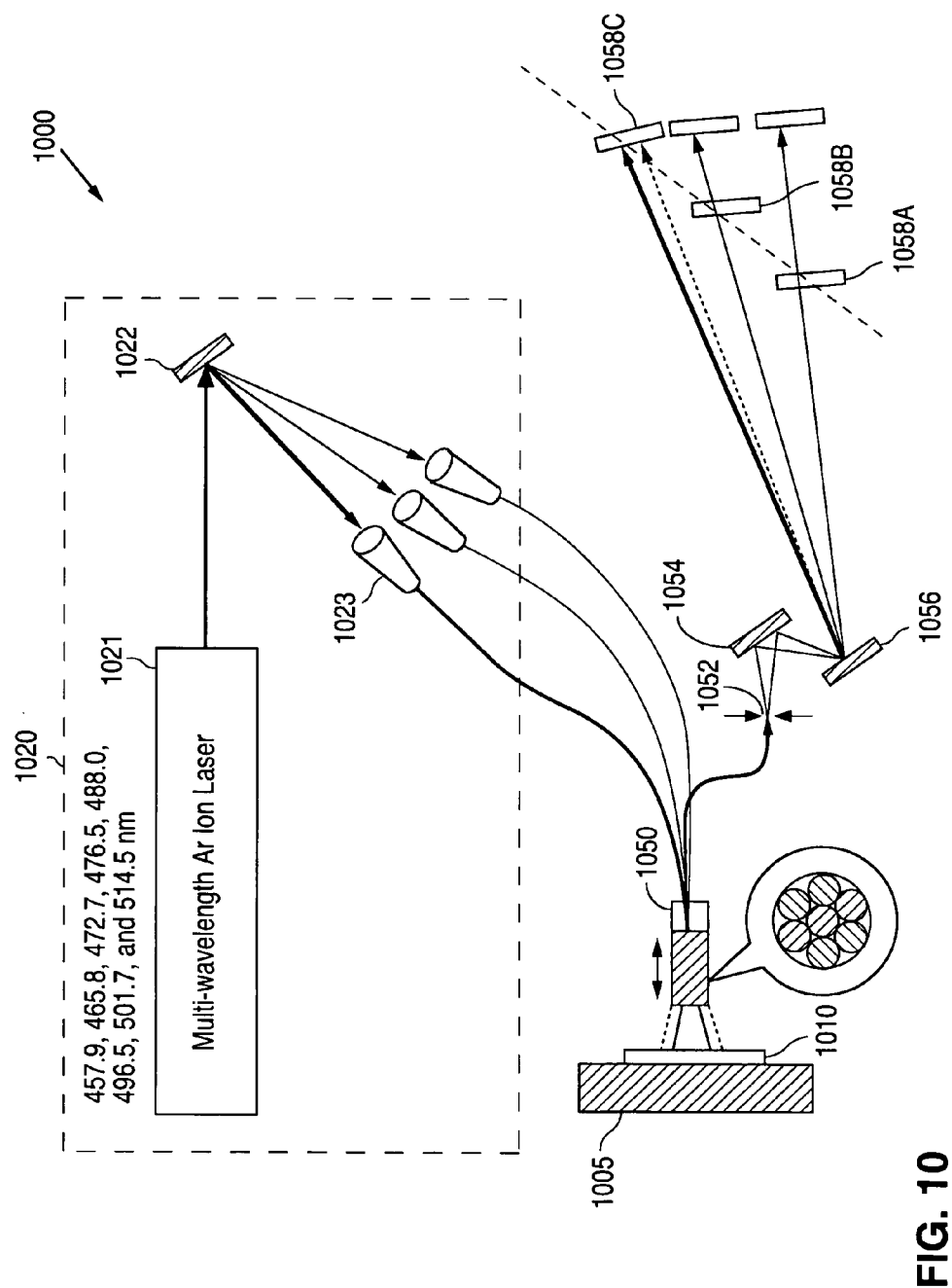
FIG. 10 is a top view of an embodiment of a spectroscopy system showing both equal distance and equal resolution configurations.

FIG. 10 shows an example of another spectroscopy system 1000 using multiple wavelength illumination of a sample 1010 positioned on a stage 1005. Stage 1005 may be an X, Y, $\theta$ stage. A light source 1020 includes a multi-wavelength argon ion laser 1021, a diffraction grating 1022 (e.g., a 1200 $mm^{-1}$ grating), and a collimating lens assembly 1023. Multiple wavelengths of light are incident on sample 1010 using optical fiber assembly 1050. Light from sample 1010, which may include reflected light and Raman scattered light, is transmitted through optical fiber assembly 1050 to a slit assembly 1052. In the illustrated embodiment, different fibers of assembly 1050 transmit light of different wavelengths to sample 1010, while one fiber transmits light from sample 1010 to slit assembly 1052.

The light is reflected using a curved focusing mirror 1054, then different wavelengths are dispersed using a dispersion element such as a diffraction grating 1056 (e.g., a 1200 $mm^{-1}$ grating). Divergent light from grating 1056 is received by detectors 1058A, 1058B, and 1058C.

The systems and techniques described herein may be configured in a number of ways. For example, FIG. 10 illustrates two different detector configurations that may be used, for particular applications. In an equal resolution configuration, detectors 1058A, 1058B, and 1058C are positioned at a distance from diffraction grating 1056 so that the resolution obtained is the same for the different wavelengths. In an equal distance configuration, detectors 1058A, 1058B, and 1058C are positioned at an equal distance from diffraction grating 1056.

Figure 11:
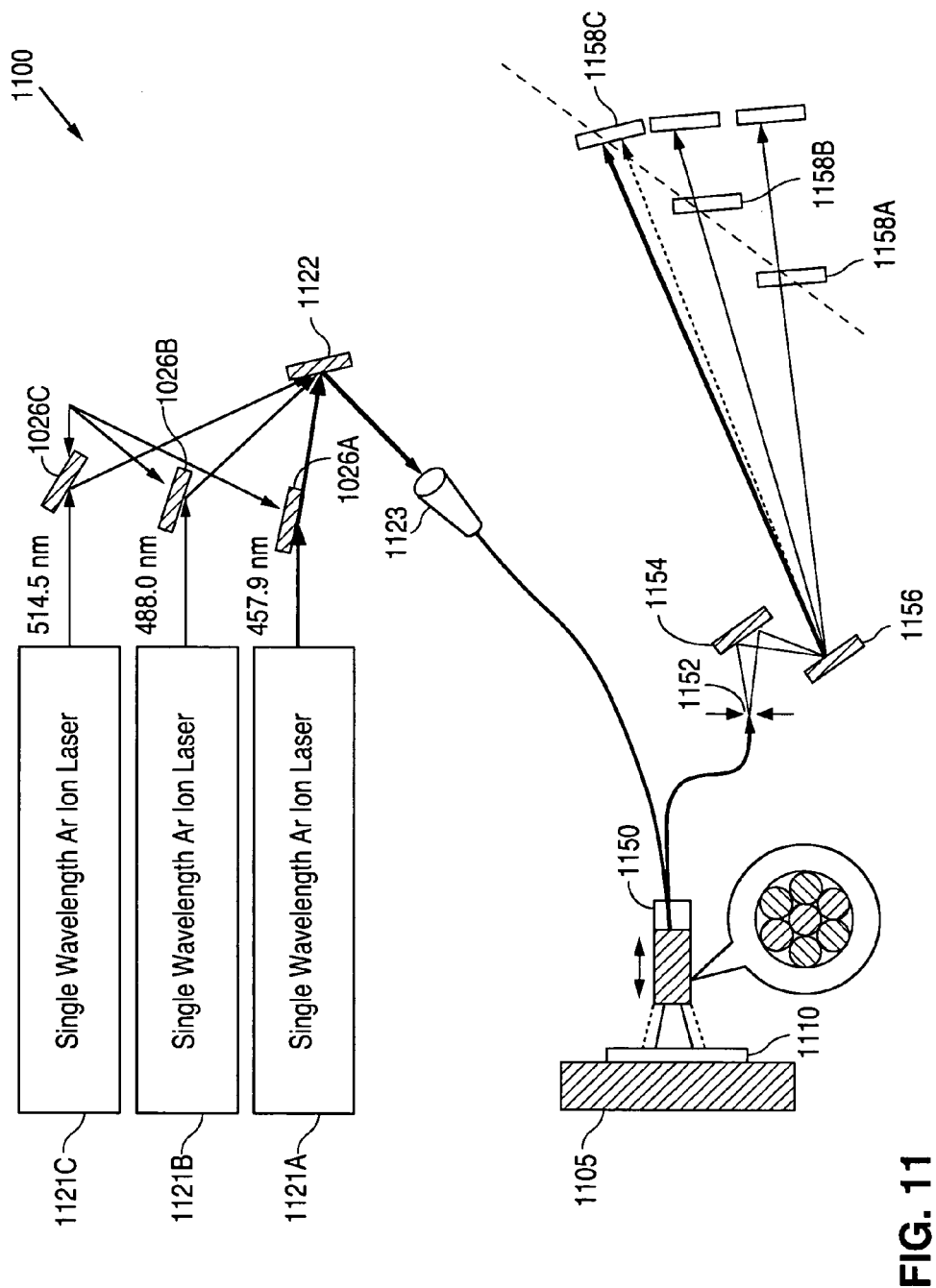
FIG. 11 is a top view of an embodiment of a spectroscopy system incorporating multiple lasers.

FIG. 11 shows an embodiment of a system 1100 incorporating different lasers to generate different wavelengths. A first argon ion laser 1121A generates light having a wavelength of 457.9 nm, while a second argon ion laser 1121B generates light having a wavelength of 488.0 nm, and a third argon ion laser 1121C generates light having a wavelength of 514.5 nm. The light is reflected to a diffraction grating 1122 (e.g., a 1200 mm$^{-1}$ grating) using optical elements 1126A, 1126B, and 1126C, which may be mirrors or diffraction gratings. As above, the light is then collimated in a collimating lens assembly 1123.

Multiple wavelengths of light are incident on sample 1110 mounted on stage 1105, using optical fiber assembly 1150. Light from sample 1110, which may include reflected light and Raman scattered light, is transmitted through optical fiber assembly 1150 to a slit assembly 1152. In the illustrated embodiment, different fibers of assembly 1150 transmit light of different wavelengths to sample 1110, while one fiber transmits light from sample 1110 to slit assembly 1152.

The light is reflected using a curved focusing mirror 1154, then different wavelengths are dispersed using a dispersion element such as a diffraction grating 1156 (e.g., a 1200 mm$^{-1}$ grating). Divergent light from grating 1156 is received by detectors 1158A, 1158B, and 1158C. FIG. 11 illustrates both an equal distance and an equal resolution configuration for the detectors.

The actual system used may be tailored for the particular spectroscopy application. For example, for a Raman spectroscopy system, a system with fixed optical elements may be desired because of its reliability. However, for other spectroscopy applications (e.g., photoluminescence applications), the range of wave numbers to be detected may be large enough that rotation of the dispersion element may be desired.

Similarly, in some applications a dispersion element may be used without other optical elements (or with just a slit or similar mechanism). Although such a system may receive more scattered light at the detector, the magnitude of the desired signal may be larger, since there is no attenuation due to the interaction of the light with additional optical elements such as mirrors and lenses. However, in some additional optical elements may provide a better signal to noise ration, despite the additional attenuation.

In implementations, the above described techniques and their variations may be implemented at least partially as computer software instructions. Such instructions may be stored on one or more machine-readable storage media or devices and are executed by, e.g., one or more computer processors, or cause the machine, to perform the described functions and operations.

A number of implementations have been described. Although only a few implementations have been disclosed in detail above, other modifications are possible, and this disclosure is intended to cover all such modifications, and most particularly, any modification which might be predictable to a person having ordinary skill in the art. For example, many types of optical elements may be used in the monochromator and spectroscopy system.

Also, only those claims which use the word "means" are intended to be interpreted under 35 USC 112, sixth paragraph. Moreover, no limitations from the specification are intended to be read into any claims, unless those limitations are expressly included in the claims. Accordingly, other embodiments are within the scope of the following claims.

What is claimed is:

1. A monochromator system, comprising:
    an optical system configured to receive light scattered from a first region of a sample surface in response to receiving light at a plurality of excitation wavelengths and to disperse the received light according to wavelength;
    a first detector mounted to a first moveable detector mount;
    a second detector mounted to a second moveable detector mount;
    wherein the first moveable detector mount is configured to move the first detector to a first position associated with a first excitation wavelength of the plurality of excitation wavelengths, and wherein the second moveable detector mount is configured to move the second detector to a second position associated with a second different excitation wavelength of the plurality of excitation wavelengths;
    and wherein a first detector configuration allows for positioning the detectors at different distances from the optical system to provide a substantially equal resolution;
    and wherein the first detector is further configured to detect a received portion of light scattered from the first region of the sample surface in response to receiving light at the first excitation wavelength at a first time, and wherein the second detector is further configured to detect a received portion of light scattered from the first region of the sample surface in response to receiving light at the second excitation wavelength at the first time.

2. The system of claim 1, wherein the optical system comprises a dispersion element selected from the group consisting of a transmissive diffraction grating, a reflective transmission grating, and a prism.

3. The system of claim 2, wherein the received portion of light scattered from the first region of the sample surface in response to receiving light at the first excitation wavelength at the first time includes divergent light.

4. The system of claim 3, wherein the received portion of light scattered from the first region of the sample surface in response to receiving light at the first excitation wavelength at the first time includes substantially parallel light.

5. The system of claim 2, wherein the first detector is further configured to receive light scattered from at least a second region of the sample surface in response to receiving light at the first excitation wavelength at the first time.

6. The system of claim 5, wherein the optical system includes a first optical fiber positioned to receive light scattered from the first region of the sample surface and a second optical fiber positioned to receive light scattered from the second region of the sample surface.

7. The system of claim 1, wherein the first detector comprises a detector selected from the group consisting of a CCD array detector, a photodiode array detector, and a CMOS detector.

8. The system of claim 1, wherein the optical system includes a flat mirror configured to reflect divergent light to be received in the first detector.

9. The system of claim 1, wherein the light scattered from the first region of the sample surface in response to receiving light at the first excitation wavelength at the first time is scattered from a portion of the first region of the sample surface extending downward a first depth, and wherein the light scattered from the first region of the sample surface in response to receiving light at the second excitation wavelength at the first time is scattered from a portion of the first region of the sample surface extending downward a second depth different than the first depth.

10. A spectroscopy method comprising: generating excitation light comprising a plurality of substantially discrete excitation wavelengths including a first excitation wavelength and a second excitation wavelength;
   scattering the excitation light from a first region of a sample;
   dispersing the scattered light according to wavelength with a disperser;
   positioning a first detector and second detector in a second configuration that positions the detectors at a substantially equal distance from the disperser;
   receiving a first portion of the dispersed light at the first detector positioned in a first configuration that allows the first detector to receive light associated with the first excitation wavelength;
   receiving a second different portion of the dispersed light at the second detector positioned in the first configuration that allows the second detector to receive light associated with the second excitation wavelength;
   and determining one or more characteristics of the first region of the sample based on the first portion and the second portion, wherein the first configuration positions the detectors at different distances from the disperser to provide a substantially equal resolution.

11. The method of claim 10, wherein the scattering the excitation light from a first region of a sample comprises scattering light having the first excitation wavelength from a first depth of the first region of the sample, and further comprises scattering light having the second excitation wavelength from a second different depth of the first region of the sample.

12. The method of claim 11, wherein determining one or more characteristics of the first region of the sample based on the first portion and the second portion comprises generating a depth profile of the first region of the sample.

13. The method of claim, 12, wherein the depth profile comprises data indicative of one or more physical characteristics of the first region of the sample at the first depth and data indicative of one or more physical characteristics of the first region of the sample at the second depth.

14. The method of claim 10, further comprising:
   prior to receiving the first portion of the dispersed light at a first detector positioned to receive light associated with the first excitation wavelength and receiving the second different portion of the dispersed light at a second detector positioned to receive light associated with the second excitation wavelength, positioning the first detector and the second detector in the first configuration that positions the detectors at different distances from the disperser, the different distances selected to provide the substantially equal resolution.

15. A system comprising:
   an optical assembly adapted to receive light scattered from a sample in response to receiving light at a plurality of excitation wavelengths and to disperse the received light according to wavelength; and
   a plurality of detector assemblies adapted to be moveable to different positions associated with a different excitation wavelengths of the plurality of excitation wavelengths,
   wherein a first configuration positions the detector assemblies at different distances from the optical assembly to provide a substantially equal resolution, and
   wherein a second configuration positions the detectors at a substantially equal distance from the optical assembly.

16. The system of claim 15, wherein the plurality of detector assemblies comprises a first detector mounted to a first moveable detector mount, and wherein the first moveable detector mount is adapted to move the first detector to a first position associated with a first excitation wavelength of the plurality of excitation wavelengths, and wherein the first moveable detector mount is linearly moveable along an optical path of light between the optical assembly and the first detector.

17. The system of claim 16, wherein the first detector is configured to detect a received portion of light scattered from the sample in response to receiving light at the first excitation wavelength.

18. The system of claim 15, wherein the plurality of detector assemblies comprises a second detector mounted to a second moveable detector mount, and wherein the second moveable detector mount is adapted to move the second detector to a second position associated with a second excitation wavelength of the plurality of excitation wavelengths, and wherein the second moveable detector mount is linearly moveable along an optical path of light between the optical assembly and the second detector.

19. The system of claim 18, wherein the second detector is configured to detect a received portion of light scattered from the sample in response to receiving light at the second excitation wavelength.

20. The system of claim 15, wherein the plurality of detector assemblies comprises a third detector mounted to a third moveable detector mount, and wherein the third moveable detector mount is adapted to move the third detector to a third position associated with a third excitation wavelength of the plurality of excitation wavelengths.

21. The system of claim 20, wherein the third detector is configured to detect a received portion of light scattered from the sample in response to receiving light at the third excitation wavelength.

* * * * *